United States Patent [19]

Nicolaou et al.

[11] Patent Number: 5,422,364
[45] Date of Patent: Jun. 6, 1995

[54] WATER SOLUBLE TAXOL DERIVATIVES

[75] Inventors: K. C. Nicolaou, La Jolla, Calif.; Claus G. Riemer, Schliengen, Germany; Michael A. Kerr, Wolfville, Canada

[73] Assignee: The Scripps Research Institute, La Jolla, Calif.

[21] Appl. No.: 122,722

[22] Filed: Sep. 16, 1993

Related U.S. Application Data

[63] Continuation-in-part of Ser. No. 940,535, Sep. 4, 1992, abandoned.

[51] Int. Cl.[6] .................. A61K 31/335; C07D 305/14
[52] U.S. Cl. .................................. 514/449; 549/510; 549/511
[58] Field of Search ................. 549/510, 511; 514/449

[56] References Cited

U.S. PATENT DOCUMENTS 4,942,184  7/1990  Haugwitz et al. .................. 514/499
4,960,790  10/1990  Stella et al. ........................ 514/499

OTHER PUBLICATIONS

Deutsch, et al., "Synthesis of Congeners and Prodrugs. 3. Water-Soluble Prodrug of Taxol with Potent Antitumor Activity", J. Med. Chem., 32: 788–792 (1989).
Swindell, et al., "Biologically Active Taxol Analogues with Deleted A-Ring Side Chain Substituents and Variable C-2' Configurations", J. Med. Chem., 34: 1176–1184 (1991).
Zhao, et al., "Modified Taxols, 6. Preparation of Water-Soluble Prodrugs of Taxol", J. of Natural Products, 54: 1607–1611 (1991).
Mathew, et al., "Synthesis and Evaluation of Some Water-Soluble Prodrugs and Derivatives of Taxol with Antitumor Activity", J. Med. Chem., 35: 145–151 (1992).

Primary Examiner—C. Warren Ivy
Assistant Examiner—Ba K. Trinh
Attorney, Agent, or Firm—Donald G. Lewis

[57] ABSTRACT

Alkaline sensitive protaxol is water soluble and is hydrolyzed at physiological (alkaline) pH to render the native taxol structure and the native taxol activity. Protaxol compositions include 2'- and/or 7-O-ester derivatives of taxol and/or 2'- and/or 7-O-carbonate derivatives taxol. Protaxol has a formula as follows:

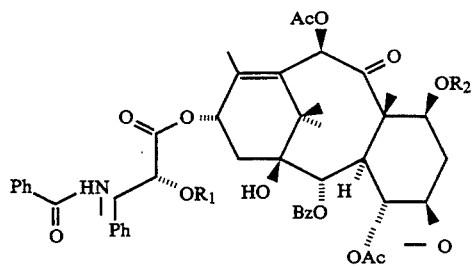

wherein $R^1$ and $R^2$ are each H or a radical selected from the group consisting of $-CO-(CH_2)_m-X-(CH_2)_n-COZ$ and $-COO-(CH_2)_o-Y-Ar$, and wherein m, n, and o are each an integer of 1 to 3; X is O, S, NH, SO, or $SO_2$; Y is S, SO or $SO_2$; Ar is phenyl or substituted phenyl wherein the substituent is halo, amino, nitro or N,N-dialkylamino having 1 to 4 carbons in each of the alkyl groups; and Z is OH, $OR^3$, $SR^3$ or $NR^4R^5$ wherein $R^3$ is alkyl containing 1 to 4 carbons and $R^4$ and $R^5$ are each alkyl containing 1 to 4 carbons, or taken together with the nitrogen to which they are attached form a saturated heterocyclic ring having 4 or 5 carbons, with the proviso that at least on $R^1$ and $R^2$ is not hydrogen; as well as the salts of such compounds with organic/inorganic bases and acids, preferably pharmaceutically acceptable salts.

13 Claims, 4 Drawing Sheets

1: TAXOL
2: TAXOTERE™

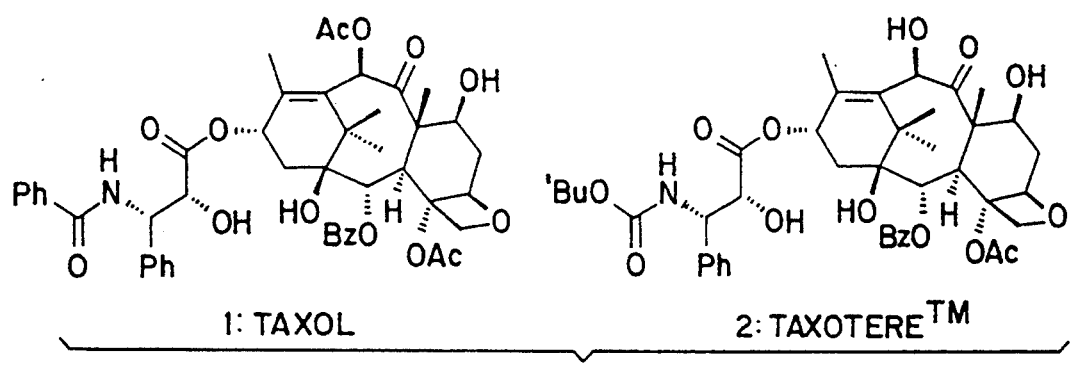
FIG. IA
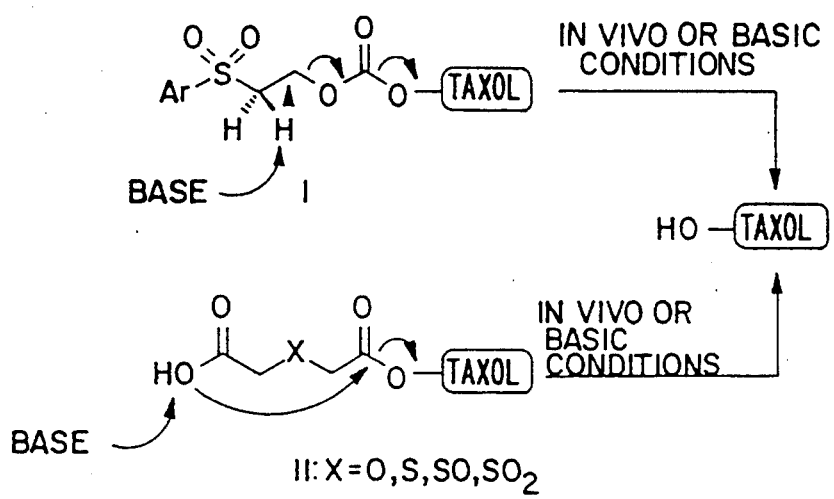
FIG. IB

WATER SOLUBLE TAXOL DERIVATIVES

This work was assisted through the financial support of the National Institutes of Health (CA 46446). Accordingly, the U.S. Government has certain rights to this invention.

CROSS-REFERENCE TO RELATED APPLICATIONS

This is a continuation-in-part of application Ser. No. 07/940,535, filed Sep. 4, 1992, now abandoned.

FIELD OF INVENTION

The invention relates to water soluble derivative of taxol which are hydrolyzable at alkaline pH and which, upon hydrolysis, possess antitumor activity against a wide variety of carcinoma cells. More particularly, this invention relates to protaxol compositions including 2'- and/or 7-O-ester derivatives and/or 2'- and/or 7-O-carbonate derivatives of taxol, pharmaceutical compositions comprising the same and methods of preparing the same.

BACKGROUND OF THE INVENTION

Taxol (1) is a natural product isolated from the Pacific yew tree (*Taxus brevifolia*). It was first isolated in 1971 from the western yew, *Taxus brevifolia* by Wani et al. (*J. Am. Chem. Soc.*, 1971, 93, 2325), who characterized its structure by chemical and X-ray crystallographic methods.

Taxol was recently approved for treatment of ovarian cancer patients. Insolubility problems with this drug, however, have prompted attempts to improve its pharmacological profile.

Taxol and various taxane derivatives (collectively herein referred to as "taxols") are highly cytotoxic and possess strong in vivo activities in a number of leukemic and tumor systems. Especially, taxol (1) is considered an exceptionally promising cancer chemotherapeutic agent, and is currently in phase II clinical trials in the United States. Equally important is taxotere (2) (L. Mangatal et al., *Tetrahedron*, 1989, 45, 4177), a semisynthetic analog of taxol which is also undergoing clinical trails with impressive results. Clinical results have demonstrated high efficacy of taxols against such cancer types as ovarian, lung, gastric, breast, colon and cervical carcinomas.

Taxol is a member of the taxane family of diterpenes having the following structure:

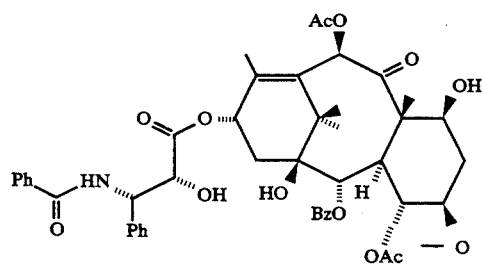

1: Taxol

A synthetic analog of taxol has the following structure:

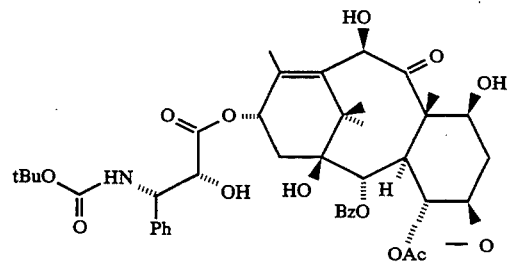

2: Taxotere ™

Taxol is only slightly soluble in water and this has created significant problems in developing suitable pharmaceutical formulations useful for chemotherapy. Some formulations of taxol for injection or I.V. infusion have been developed utilizing CREMOPHOR EL ® (polyoxyethylated castor oil) as the drug carrier because of taxol's aqueous insolubility. For example, taxol supplied by the NCI has been formulated in 50% CREMOPHOR EL ® and 50% dehydrated alcohol. CREMOPHOR EL ®, however, is itself toxic and produces, when given in a large volume single dose without taxol, vasodilation, labored breathing, lethargy, hypotension and death in dogs. Therefore, the use of this carrier would not be recommended.

In an attempt to increase taxol's solubility and to develop more safe clinical formulations, studies have been directed to synthesizing taxol analogs where 2'- and/or 7-position is derivatized with groups that would enhance water solubility. These efforts yielded protaxol compounds that are more water soluble than the parent compound and that deplay the cytotoxic properties upon activation.

U.S. Pat. No. 4.942.184 to R. D. Haugwitz, et al. discloses water soluble taxols having variously substituted acyl groups at 2'-O-position.

U.S. Pat. No. 4.960.790 to V. J. Stella, et al. discloses water soluble taxols the 2'- and/or 7-hydroxyl of which is derivatized with a selected amino acid or an amino acid mimetic compound.

Structure-activity relationships and solubility improvements of taxol have been probed through substitution at the C-2' hydroxyl group. For example, H. M. Deutsch et al. disclosed the synthesis of water-soluble prodrugs of Taxol with potent antitumor activity, *Journal of Medical Chemistry* (1989) 32, 788–792. More recent efforts to this end were also disclosed by Charles Swindell et al. (Journal of Medical Chemistry (1991) 34, 1176–1184), by Zhiyang Zhao et al. (*Journal of Natural Products* (1991) 54, 1607–1611) and by Abraham E. Mathew et al. (*Journal of Medical Chemistry* (1992) 35, 145–151). However, none of the prodrugs disclosed in the prior art exhibited sensitivity to alkaline hydrolysis under physiological conditions. This absence of sensitivity compromises their utility as pharmacological agents.

Accordingly, it is apparent that it would have been desirable to develop protaxol derivatives which would be more water soluble than taxol, but which, upon hydrolysis under physiological (alkaline) conditions, would exhibit the same or similar level of antitumor activity as unmodified taxol. Furthermore, the rate of hydrolysis should facilitate the pharmacokinetics of the drug so as to enhance its delivery. The present invention achieves this goal by providing protaxol derivatives that are water soluble and that are susceptible, under physiological conditions, to a novel mechanism of controlled hydrolysis for providing the bioactive form of taxol at a pharmacokinetically favorable rate.

SUMMARY OF THE INVENTION

A series of taxol-releasing compounds (protaxols) with improved properties are synthesized and demonstrated to have enhanced biological activity. These prodrugs are designed on the basis of chemical principles to allow for in vitro and in vivo taxol release under basic or physiological conditions. Chemical studies demonstrate the stability of these compounds at pH greater than 7 and the ability of these compounds to release taxol in basic media. Biological investigations confirm the taxol-like activity of these prodrugs as microtubule stabilizing agents. Studies with tumor cell lines reveal cytotoxic properties comparable to those of taxol, whereas incubation with human blood plasma confirm rapid taxol release. These results demonstrate the potential of such designed compounds as anticancer agents with improved profiles as compared to those of taxol and Taxotere (2).

Organic chemistry concepts are employed as guiding principles to rationally designed two types of structures (FIG. 1B). Recognizing that the C-2' hydroxyl group is the most convenient site to attach designed functional domains and realizing that blocking this position would result in loss of activity, groups fulfilling the following criteria are selected:

(a) The functional group must initiate its own cleavage from the conjugate and must generate taxol in situ upon suitable activation; and (b) The newly introduced group must increase the water solubility of the compound.

Since certain drug-resistant tumor cells exhibit basic pH microenvironments, base labile moieties are preferred as activating groups. Both types of appendages illustrated in structures I and II are cleaved either by basic conditions or via enzymatic assistance as indicated in FIG. 1B.

Protaxol compounds belonging to the Type I group include a water soluble functional group having a carbonate ester attached to the C-2' position of taxol. The water soluble functional group is connected to the C-2' position by means of a carbonate ester. Also connected to the carbonate ester is an electron withdrawing aryl substituent. Under physiological conditions, the rate of taxol activation of Type I compounds increases with the electron withdrawing ability of the aryl substituent. As illustrated in FIG. 1B, hydrolysis may be induced by physiological or alkali conditions and proceeds with an elimination reaction resulting in the release from the carbonate ester of both the aryl substituent and the taxol. Activation of protaxols from Type I compounds necessarily results in the evolution of $CO_2$.

Protaxol compounds belonging to Type II group include a water soluble functional group attached by means of an ester linkage to the C-2' position of taxol. The distal end of the water soluble functional group includes a carboxylic group. Between the carboxylic group at the distal end and the ester linkage adjacent to the taxol is an electron withdrawing heteroatom or group. Under physiological (alkaline) conditions, the water soluble functional group undergoes a cyclization involving the formation of an anhydride or anhydride intermediate. The rate of hydrolysis and taxol activation increases with the electron withdrawing nature of the linking heteroatom.

It is, therefore, an object of the present invention to provide taxol derivatives (protaxol) with enhanced water solubility while retaining the ability to reconstitute or re-activate the parent taxol and its cytotoxic properties.

It is another object of the present invention to provide methods of preparing water soluble derivatives of taxol with antitumor activity.

It is a further object of the present invention to provide a method of treating tumors in a mammal by administration of water soluble derivatives of taxol.

It is another object of the present invention to provide methods for converting protaxol to taxol.

It is a still further object of the present invention to provide a pharmaceutical composition comprising an effective antitumor amount of water soluble derivatives of taxol as an active ingredient and a pharmaceutically acceptable carrier.

BRIEF DESCRIPTION OF THE DRAWINGS

FIG. 1A illustrates the molecular structure of taxol and Taxotere (TM).

FIG. 1B illustrates the mechanistic rationale for the design of protaxols.

DETAILED DESCRIPTION OF THE INVENTION

The taxol derivatives 5–14 illustrated in Table 1A were designed and synthesized on the basis of the above considerations. The carbonates were prepared via derivatization with an appropriate (2-thioaryl)ethyl chloroformate while the esters were formed by reaction with a suitable anhydride. Further manipulations yielded additional compounds for testing.

The solubilities of the synthesized protaxols in $D_2O$ were determined by 1H NMR spectroscopy. These studies revealed considerably higher solubilities (Table 1A) than taxol for compounds of type II while compounds of type I (FIG. 1B) showed little improvement in water solubility as compared to taxol.

Figure 2A:
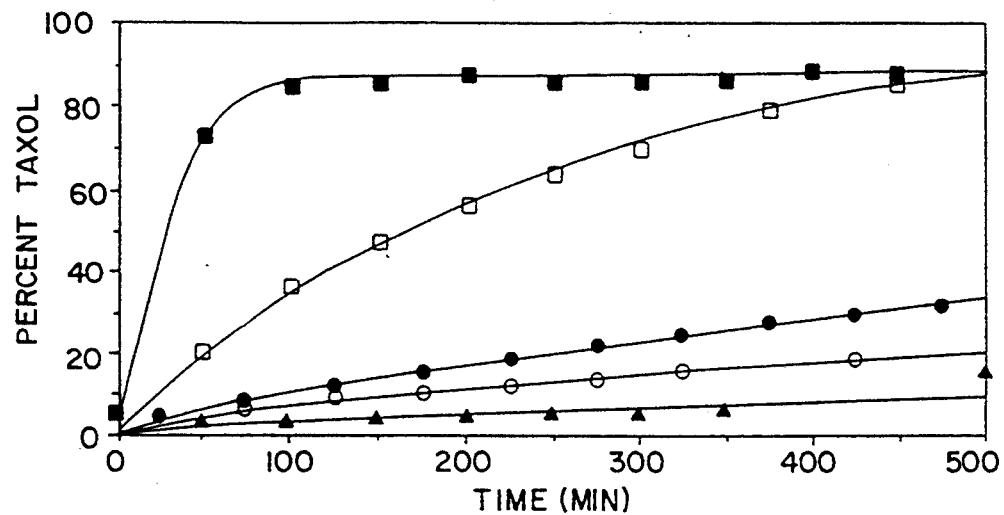
FIG. 2A illustrates the kinetics of taxol release from protaxol 5 in aqueous buffer solutions at various pH's and temperatures.

All designed compounds exhibited excellent stability in aprotic organic solvents and in the solid state. However, in aqueous media, some of these compounds showed tendencies to slowly revert to taxol even at pH 7.0. The derivatives in which the C-7 hydroxyl group was acetylated were extremely unstable in aqueous media losing the C-7 substituent very rapidly. The stability of the synthesized compounds was examined at various pH's and temperatures. FIG. 2A summarizes such a study carried out with compound 5 in which the accelerating effect of higher temperatures and pH on taxol release was demonstrated. Table 1A includes the half-lives of six of these compounds at pH 7.5 and 9. As seen from these data, for compounds of type I, the rate of taxol release increases with the electron withdrawing ability of the aryl substituents, whereas for type II derivatives, the rate of release increases with the electron withdrawing nature of the linking heteroatom. This illustrates the ability to fine-tune the rate of release of taxol to a desired set of conditions using simple chemical principles.

TABLE 1

Designed protaxols and their solubility and stability properties (A) and cytotoxicity data for selected compounds (B).

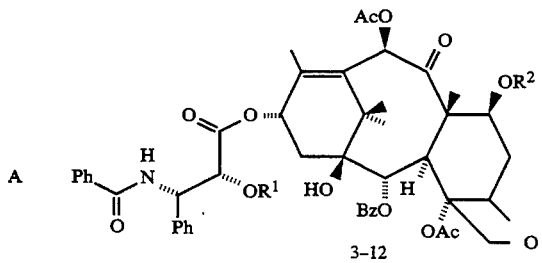

| Compound | | Water solubility (mg/mL)$^k$ | $t_{\frac{1}{2}}{}^n$ (pH 7.5) | $t_{\frac{1}{2}}{}^n$ (pH 9) |
|---|---|---|---|---|
| 1: taxol: $R^1 = R^2 = H$ | | <<0.10 | | |
| $3^a$: $R^1 =$ (structure) | $R^2 = H$ | 0.84 | >500 | 110 |
| $4^b$: $R^1 =$ (structure) | $R^2 = H$ | 0.35 | >500 | 300 |
| $5^c$: $R^1 =$ (structure) | $R^2 = H$ | 1.2$^m$ | >500 | 30 |
| $6^d$: $R^1 =$ (structure) | $R^2 = H$ | — | — | — |
| $7^e$: $R^1 =$ (structure) | $R^2 = H$ | — | — | — |
| $8^f$: $R^1 =$ (structure) | $R^2 = H$ | <0.10$^l$ | >500 | 66 |
| $9^g$: $R^1 =$ (structure) | $R^2 = H$ | <0.10$^l$ | >500 | 7 |
| $10^h$: $R^1 =$ (structure) | $R^2 = H$ | <0.10$^l$ | >>500 | 101 |
| $11^i$: $R^1 = R^2 =$ (structure) | | — | 0.50 | — | — |
| $12^j$: $R^1 = R^2 =$ (structure) | | — | 0.46 | — | — |

TABLE 1 B

Cytotoxicity of taxol derivatives (IC$_{50}$[M])*

TABLE 1 B-continued

| Normal Cell lines | Against Normal Cell Lines Compounds: | | | |
|---|---|---|---|---|
| | | Taxol (1) | 5 | 6 | 7 |
| NHDF Normal human skin RPMI-7666 | | 10$^{-6}$ | 10$^{-6}$ | 10$^{-6}$ | 10$^{-6}$ |

TABLE 1 B-continued

| | | | | |
|---|---|---|---|---|
| Normal human PBLs BALB/c 3T3 | $10^{-4}$ | $10^{-4}$ | $10^{-4}$ | $10^{-4}$ |
| Normal mouse embryo CHO | $10^{-6}$ | $10^{-5}$ | $10^{-5}$ | $10^{-5}$ |
| Chinese hamster ovary CHO | $10^{-4}$ | $10^{-4}$ | $10^{-4}$ | $10^{-4}$ |
| Normal human mammary | $10^{-4}$ | $10^{-4}$ | $10^{-4}$ | $10^{-4}$ |

| Normal Cell lines | Compounds: | | | |
|---|---|---|---|---|
| NHDF | 9 | 10 | 11 | 12 |
| Normal human skin RPMI-7666 | $10^{-6}$ | $10^{-6}$ | $10^{-6}$ | $10^{-6}$ |
| Normal human PBLs BALB/c 3T3 | $10^{-4}$ | $10^{-4}$ | $10^{-4}$ | $10^{-4}$ |
| Normal mouse embryo CHO | $10^{-5}$ | $10^{-5}$ | $10^{-6}$ | $10^{-5}$ |
| Chinese hamster ovary CHO | $10^{-4}$ | $10^{-4}$ | $10^{-4}$ | $10^{-4}$ |
| Normal human mammary | $10^{-4}$ | $10^{-4}$ | $10^{-4}$ | $10^{-4}$ |

Cytotoxicity of taxol derivatives ($IC_{50}[M]$)*
Against Cancer Cell Lines

| Cancer cell lines | Compounds: | | | |
|---|---|---|---|---|
| SK | Taxol (1) | 5 | 6 | 7 |
| Melanoma Capan-1 | $10^{-5}$ | $10^{-5}$ | $10^{-5}$ | $10^{-5}$ |
| Pancreatic H322 | $<10^{-9}$ | $<10^{-9}$ | $10^{-7}$ | $<10^{-9}$ |
| Lung carcinoma MCF-7 | $10^{-9}$ | $10^{-9}$ | $10^{-7}$ | $10^{-9}$ |
| Breast carcinoma BT-549 | $<10^{-5}$ | $10^{-5}$ | $10^{-5}$ | $10^{-5}$ |
| Breast carcinoma OVCAR-3 | $10^{-9}$ | $<10^{-9}$ | $10^{-9}$ | $<10^{-9}$ |
| Ovarian carcinoma HT-29 | $<10^{-9}$ | $<10^{-9}$ | $10^{-6}$ | $<10^{-9}$ |
| Colon carcinoma SIHA | $<10^{-9}$ | $<10^{-9}$ | $10^{-7}$ | $<10^{-9}$ |
| Cervix carcinoma 786-0 | $10^{-5}$ | $10^{-4}$ | $10^{-4}$ | $10^{-5}$ |
| Renal cell carcinoma PC-3 | $10^{-7}$ | $10^{-6}$ | $10^{-5}$ | $10^{-5}$ |
| Prostate carcinoma HL-60 | $10^{-6}$ | $10^{-6}$ | $10^{-6}$ | $10^{-6}$ |
| Promyel carcinoma MOLT-4 | $<10^{-9}$ | $<10^{-9}$ | $10^{-7}$ | $<10^{-9}$ |
| T-cell leukaemia L1210 | $<10^{-9}$ | $10^{-9}$ | $10^{-7}$ | $<10^{-9}$ |
| Mouse leukaemia UCLA-P-3 | $10^{-6}$ | $10^{-5}$ | $10^{-5}$ | $10^{-5}$ |
| Lung carcinoma | $<10^{-9}$ | $<10^{-9}$ | $<10^{-9}$ | $<10^{-9}$ |

| Cancer cell lines | Compounds: | | | |
|---|---|---|---|---|
| SK | 9 | 10 | 11 | 12 |
| Melanoma Capan-1 | $10^{-5}$ | $10^{-5}$ | $10^{-5}$ | $10^{-5}$ |
| Pancreatic H322 | $10^{-6}$ | $<10^{-9}$ | $<10^{-9}$ | $<10^{-9}$ |
| Lung carcinoma MCF-7 | $10^{-6}$ | $10^{-8}$ | $10^{-9}$ | $10^{-7}$ |
| Breast carcinoma BT-549 | $10^{-5}$ | $10^{-5}$ | $10^{-5}$ | $10^{-5}$ |
| Breast carcinoma OVCAR-3 | $10^{-7}$ | $10^{-7}$ | $<10^{-9}$ | $<10^{-9}$ |
| Ovarian carcinoma HT-29 | $10^{-6}$ | $<10^{-9}$ | $10^{-6}$ | $10^{-8}$ |
| Colon carcinoma SIHA | $10^{-7}$ | $<10^{-9}$ | $<10^{-9}$ | $10^{-7}$ |
| Cervix carcinoma 786-0 | $10^{-5}$ | $10^{-5}$ | $10^{-5}$ | $10^{-5}$ |
| Renal cell carcinoma PC-3 | $10^{-6}$ | $10^{-6}$ | $10^{-6}$ | $10^{-6}$ |
| Prostate carcinoma HL-60 | $10^{-6}$ | $10^{-6}$ | $10^{-6}$ | $10^{-6}$ |
| Promyel carcinoma MOLT-4 | $10^{-7}$ | $<10^{-9}$ | $<10^{-9}$ | $<10^{-9}$ |
| T-cell leukaemia | $10^{-9}$ | $<10^{-9}$ | $<10^{-9}$ | $<10^{-9}$ |

TABLE 1 B-continued

| | | | | |
|---|---|---|---|---|
| L1210 Mouse leukaemia UCLA-P-3 | $10^{-6}$ | $10^{-5}$ | $10^{-6}$ | $10^{-6}$ |
| Lung carcinoma | $<10^{-9}$ | $<10^{-9}$ | $10^{-9}$ | $10^{-9}$ |

Figure 2B:
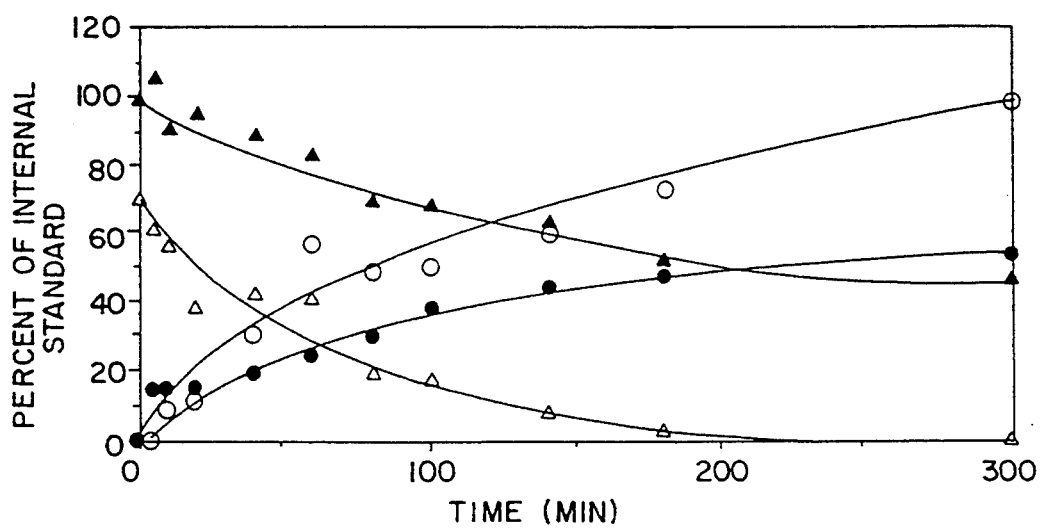
FIG. 2B illustrates the kinetics of taxol release from protaxol 5 in human blood plasma and pH 7.4 buffer solution at 37° Centigrade.

Significantly, incubation of compound 5 in human blood plasma at 37° Centigrade demonstrates accelerated release of taxol, with a half-life ($t_{\frac{1}{2}}$) of approximately 100 minutes, as compared to the slower rate of taxol release in aqueous media under the same conditions of pH and temperature (FIG. 2B). This finding supports the chemical assistance for taxol release from this compound (5) by factors present in human blood plasma and raises expectations for in vivo efficacy of this compound.

Figure 3A:
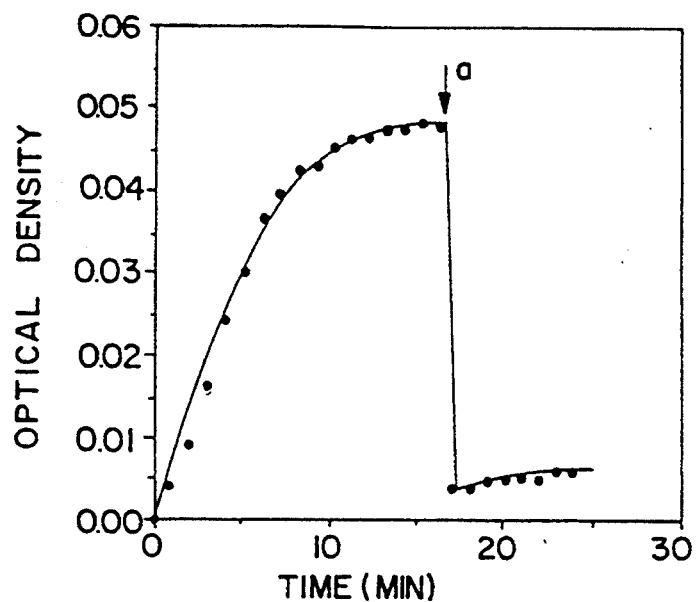
FIG. 3 illustrates the tubulin polymerization-depolymerization measurements with taxol and designed protaxol 5.
Figure 3B:
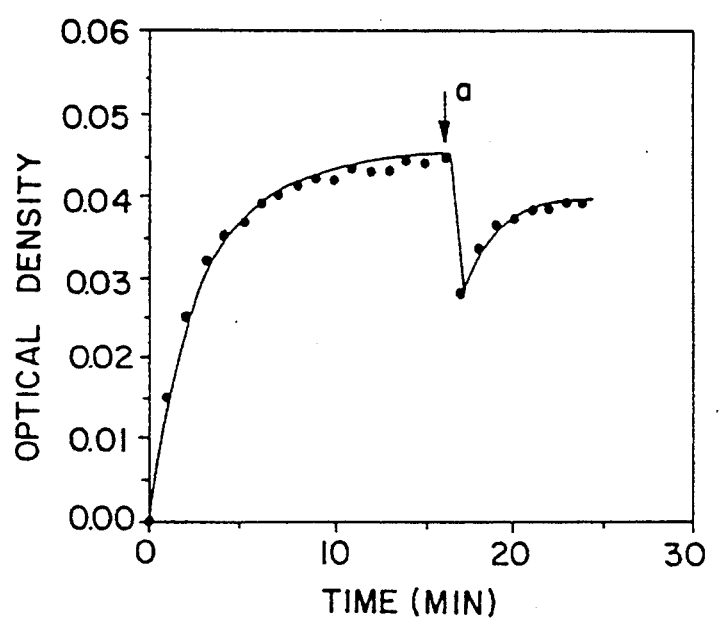
Figure 3C:
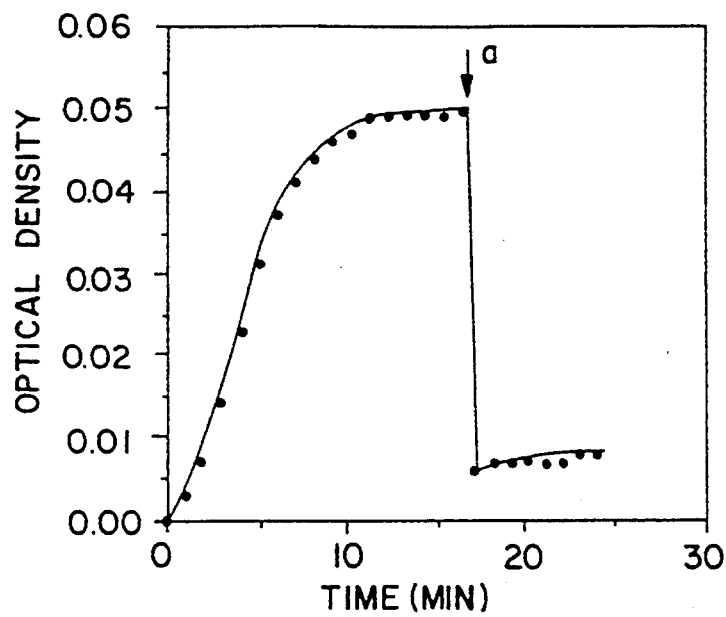
Figure 3D:
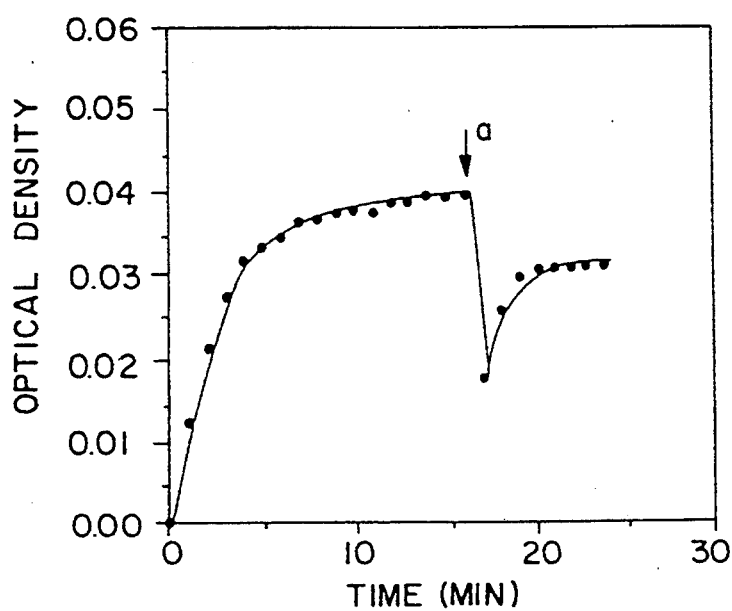

Tubulin polymerization to microtubules is promoted by GTP, whereas CaCl2 causes depolymerization of microtubules back to tubulin (FIG. 3A). Taxol allows and promotes this type of microtubule assembly and, furthermore, it stabilizes microtubules against CaCl2-induced depolymerization (FIG. 3B). The designed protaxol 5 was tested for its ability to stabilize microtubules formed from tubulin via the action of GTP. This agent failed to prevent CaCl2-induced disassembly of microtubules at the initial stages of the experiment (FIG. 3C), but showed increased potency with prolonged exposure times as expected from the slow release of taxol, and reached potencies comparable to that of taxol when essentially complete conversion to taxol had occurred (FIG. 3D). Similar results were obtained with a number of other designed taxols shown in Table 1. These findings are in agreement with the previously reported loss of activity resulting from blocking the C-2' hydroxyl group.

The protaxols synthesized in this study were tested against a broad spectrum of cell lines ranging from the multiple-drug resistant ovarian (OVCAR-3) to lung (H-322) and leukemia (MOLT-4) cells in order to assess cytotoxicity, cell-type selectivity, and duration of action. Comparisons with taxol itself revealed not only similar potencies but also similar selectivities against various cell lines. This is consistent with a mechanism of action involving taxol release rather than the derivative itself exhibiting intrinsic activity. Furthermore, taxol was isolated and characterized from aqueous solutions of the designed compounds, thus firmly establishing the release of the agent under the conditions of the microtubule assembly and cytotoxicity experiments. The most significant findings are shown in Table 1B. As demonstrated by these results, the rather impressive selectivity of taxol against cancer cells versus normal cells is maintained in the designed compounds. Noteworthy are the lower cytotoxicities of compounds 6 and 9 after a three-day exposure which are in line with the lower rates of release of taxol from these conjugates.

The results presented herein demonstrate the power of chemical principles in the molecular design of fine-tuned derivatives of the taxol family for biological and pharmacological studies. The designed molecules act as prodrugs, releasing the active agent in situ as shown by chemical studies. Investigations with tubulin and in vitro cytotoxicity experiments confirmed the unique taxol-like profiles of a number of these compounds. Particularly promising is compound 5 which exhibited good solubility and stability properties in aqueous media while rapidly releasing taxol in human blood plasma. Issues remaining to be addressed include further pharmacological studies with these compounds and the design and synthesis of more potent and selective compounds as well as effective agents against resistant-type tumors. Such agents may be arrived at by modifications of naturally occurring compounds or by total synthesis.

Accordingly, the present invention is directed to novel taxol derivatives having the general formula (I):

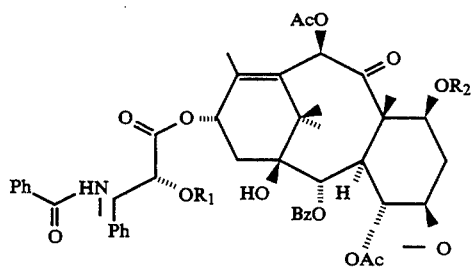

wherein $R^1$ and $R^2$ are each H or a radical selected from the group consisting of $-CO-(CH_2)_m-X-(CH_2)_n-COZ$ and $-COO-(CH_2)_o-Y-Ar$, wherein m, n, and o are each an integer of 1 to 3; X is O, S, NH, SO, or $SO_2$; Y is S, SO or $SO_2$; Ar is phenyl or substituted phenyl wherein the substituent is halo, amino, nitro or N,N-dialkylamino having 1 to 4 carbons in each of the alkyl groups; and Z is OH, $OR^3$, $SR^3$ or $NR^4R^5$ wherein $R^3$ is alkyl containing 1 to 4 carbons and $R^4$ and $R^5$ are each alkyl containing 1 to 4 carbons, or taken together with the nitrogen to which they are attached form a saturated heterocyclic ring having 4 or 5 carbons, with the proviso that at least one of $R^1$ and $R^2$ is not hydrogen; as well as the salts of such compounds with organic/inorganic bases and acids, preferably pharmaceutically acceptable salts.

The expression "saturated heterocyclic ring having 4 or 5 carbons" used herein refers to groups such as 1-pyrrolidinyl, 1-piperidinyl, 1-morpholino, 1-thiomorpholino.

The present invention includes (a) derivatives esterified at the 2'-hydroxyl group of taxol, (b) derivatives esterified at the 7-hydroxyl group of taxol, and (c) derivatives esterified at both the 2'- and 7-position hydroxyl groups.

In the above formula (I) preferred values for $R^1$ and $R^2$ are $-CO-CH_2-X-CH_2-COOH$ wherein X is as previously defined. Other preferred values are $-COO-(CH_2)_2-Y-C_6H_5$ wherein Y is as previously defined.

Thus, a first preferred group of compounds of the present invention are those wherein $R^2$ is H and $R^1$ is $-CO-CH_2-X-CH_2-COOH$ wherein X is as previously defined.

A second preferred group of compounds of the present invention are those wherein each of $R^1$ and $R^2$ is $-CO-CH_2-X-CH_2-COOH$ wherein X is as previously defined.

A third preferred group of compounds of the present invention are those wherein $R^2$ is hydrogen and $R^1$ is $-COO-(CH_2)_2-Y-C_6H_5$ wherein Y is as previously defined.

These novel derivatives of formula (I) may be prepared by esterifying taxol with an appropriate acid $HO-CO-(CH_2)_m-X-(CH_2)_n-COZ$ or a haloformate of $Hal-COO-(CH_2)_o-Y-Ar$ wherein X, Y, Z, and Ar are as previously defined and Hal is halo. The acid is normally activated prior to reaction with taxol, involving formation of a symmetric anhydride, mixed anhydride, activated ester, acid chloride or the like. Particularly preferred acid reagents used in the present invention are diglycolic anhydride and thiodiglycolic anhydride. The activation step can be carried out by various condensing agents, such as carbonyldiimidazole, dicyclohexylcarbodiimide, hydroxybenzotriazole and the like. Alternatively, the esterification between taxol and the acid can be conducted in the presence of such condensing agents.

The esterification may be facilitated by addition of a catalyst such as pyridine, 4-N,N-dimethylaminopyridine (DMAP) or triethylamine although the catalyst is not always required.

Thus, the esterification is conducted in a reaction-inert solvent in the presence of a condensing agent (if no prior activation of an acid is involved) with or without the additional presence of a catalyst at a temperature of from 0° to about 100° C., preferably at ambient temperature.

Suitable reaction-inert solvents which can be used in the esterification are aprotic solvents such as N,N-dimethylformamide, N,N-dimethylacetamide, N-methylpyrolidone, and hexamethyl phosphoramide; aromatic solvents such as benzene, toluene, xylene, ethylbenzene, and chlorobenzene; chlorinated hydrocarbons, such as chloroform and dichloromethane; ethers, such as diethyl ether and tetrahydrofuran; low molecular weight esters, such as ethyl acetate and butyl acetate; low molecular weight aliphatic ketones, such as acetone and methyl ethyl ketone, and mixture thereof. It is, however, especially advantageous to use pyridine as the solvent, since it also catalyzes the esterification step.

In practice taxol is usually treated with an excess of the acid or the haloformate, preferably 3 to 10 moles of each per mole of taxol. The reaction time varies according to a number of factors, but at about 25° C. reaction times from 0.5 to 24 hours are commonly used. The compounds of formula (I) can be isolated and purified by conventional methods known in the art, e.g., chromatography.

Since the 2'-hydroxyl of taxol is more reactive than the 7-position hydroxyl, the 2'-position is esterified first. Thus, the above esterification leads to the compounds of formula (I) wherein $R^1$ is other than hydrogen, i.e. 2'-O-ester derivatives. When more than 2 equivalents of the acid or the haloformate are used in the reaction, the esterification may provide 2'-, 7-disubstituted taxol derivatives. Although the esterification at the 2'-position can be conducted with or without a catalyst, the esterification at the 7-position may require the presence of a catalyst due to the reduced chemical reactivity of the 7-hydroxyl of taxol.

For the preparation of 7-O-esters of taxol, the 2'-hydroxyl must be protected or blocked, then the 7-hydroxyl is esterified and further the 2'-protecting or blocking group is removed. A wide variety of hydroxyl protecting groups can be employed for this purpose. Exemplary of such protecting groups are trialkylsilyl where each alkyl contains 1 to 5 carbons, methoxymethyl, 1-ethoxyethyl, benzyloxymethyl, tetrahydropyranyl, and 2,2,2-trichloroethoxy-carbonyl.

The reaction between 2'-protected taxol and the esterifying agent proceeds in essentially the same manner as described above. The protecting groups can then be removed by appropriate means known in the art (e.g.

mild acid, mild base, treatment with fluorides or hydrogenolysis).

The starting acids HO—CO—(CH$_2$)$_m$—X—(CH$_2$)$_n$—COZ and the haloformate Hal—COO—(CH$_2$)$_o$—Y—Ar are either known compounds or may be prepared by methods reported in the prior art.

In the case of compounds of formula (I) wherein Z is other than hydroxyl, they can conveniently be prepared by reacting acids of formula (I) wherein Z is OH with an appropriate amine (H$_2$NR$^4$R$^5$), alcohol, (R$^3$OH) or thiol (R$^3$SH).

Compounds of formula (I) wherein X and Y are each SO or SO$_2$ can be obtained from compounds of formula (I) wherein X and Y are each S or SO by means of oxidation. Oxidants which can be employed in this oxidation include peracids such as peracetic acid, perbenzoic acid, m-chloroperbenzoic acid, and monoperphthalic acid, hydrogen peroxide, periodic acids such as paraperiodic acid, and sodium periodate, and inorganic oxidants such as potassium monopersulfate.

The oxidation can be carried out in a reaction inert solvent at a temperature of from 0° to about 50° C. Suitable solvents include dichloromethane, chlorform and lower alcohols (methanol or ethanol). When potassium monopersulfate is used as the oxidant, the oxidation reaction may be carried out in an aqueous medium utilizing a water miscible solvent such as methanol. The reaction times are in the range of about 0.5 to 24 hours. For one mole of the reactant, it is preferred to use at least one molar equivalent of the oxidant. For the preparation of the sulfone, the use of an excess amount of the oxidant is desirable. The sulfones can be obtained simply by adding excess oxidant to a solution of the crude sulfoxide formed and allowing oxidation to completion. Alternatively, the sulfoxides can be prepared directly from the thio compounds of formula (I) wherein X or Y is S using excess oxidant.

The product sulfoxide or sulfone can be isolated and purified by conventional methods known in the art, e.g., chromatography.

The oxidation may produce a mixture of sulfone and sulfoxide. By proper choice of molar ratios and reaction conditions, the reaction may be stopped at the sulfoxide stage. Thus, the selective preparation of sulfoxides of formula (I) wherein X or Y is SO is possible. Also, a disastereomic mixture of the sulfoxide of formula (I) wherein X or Y is SO will result from the above oxidation reaction. If desired, the diasteromers can be separated by column chromatography, since they differ markedly in polarity. These diastereomers are to be considered within the scope and purview of the present invention.

Compounds of formula (I) wherein Z is OH, have a carboxyl group and therefore they will form pharmaceutically acceptable salts with inorganic and organic bases. These base salts are prepared by standard methods, for example by contacting the acidic and basic components in a stoichiometric ratio, in an aqueous, non-aqueous or partially aqueous medium, as appropriate. They are then recovered by filtration, by precipitation with a non-solvent followed by filtration, by evaporation of the solvent, or, in the case of aqueous solutions, by lyophilization, as appropriate. Illustrative are the ammonia salt, alkali salts, and organic amine salts which are preferred. Examples of the organic amine salts include trimethylamine, triethylamine, triethanolamine, N-methyl-N,N-diethanolamine, N-methylglucamine.

Compounds of formula (I) having an amino or N,N-dialkylamino group may form pharmaceutically acceptable salts with inorganic and organic acids. Of particular value are the sulfate, hydrochloride, hydrobromide, nitrate, phosphate, citrate, tartrate, pamoate, perchlorate, sulfosalicylate, benzenesulfonate, 4-toluenesulfonate, and 2-naphthalenesulfonate salts.

The taxol derivatives of formula (I) can be utilized in the treatment of tumors in a mammal due to their cytotoxic, antitumor activity. These compounds can be administered to a mammal, particularly human by either the oral or parenteral routes of administration.

Where gastrointestinal absorption permits, oral administration is preferred for reasons of patient convenience and comfort. In general, these taxol derivatives are normally administered in dosages ranging from about 0.1 mg to about 10 mg per kg of body weight per day; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

For parenteral use, the present compounds are formulated according to the known art using suitable dispersing or wetting agents and suspending agents. The sterile injectable formulation can also be a solution of suspension in a non-toxic parenterally acceptable diluent or solvent, for example, as a solution in 1,3-butandiol. Among the acceptable vehicles and solvents are water, Ringer's solution and isotonic NaCl solution, fixed oils including synthetic mono-or di-glycerides, fatty acids such as oleic acids, and mixtures thereof.

For oral administration, a wide variety of dosage forms are used, e.g., tablets, capsules, lozenges, trochees, hard candies, powders, syrups, aqueous suspension, elixirs, syrups, and the like formulated with various pharmaceutically-acceptable inert carriers. Such carriers include solid diluents or fillers, sterile aqueous media and various non-toxic organic solvents, etc. In general, the compounds of the present invention are present in such oral dosage forms at concentration levels ranging from about 0.5% to about 90% by weight of the total composition, in amounts which are sufficient to provide the desired unit dosage. Tablets may contain various excipients such as sodium citrate, calcium carbonate and calcium phosphate, along with various disintegrants such as starch (preferably potato or tapioca starch), alginic acid and certain complex silicates, together with binding agents such as polyvinylpyrrolidione, sucrose, gelatin and acacia. Additionally, lubricating agents such as magnesium stearate, sodium lauryl sulfate and talc are often very useful for tabletting purposes. Solid compositions of a similar type may also be employed as filters in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various like combinations thereof.

The present compounds can also be administered in the form of liposomes. As is known in the art, liposomes are generally derived from phospholipids or other lipid substances. Liposomes are formed by mono-or multi-lamellar hydrated liquid crystals that are dispersed in an aqueous medium. Any non-toxic, pharmaceutically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, *Methods in Cell Biology;* Prescott, Ed; Academic: New York, 1976, Vol. XIV.

Additional pharmaceutical methods may be employed to control the duration of pharmacological action. Controlled release preparations may be achieved by the use of polymers to complex or adsorb the present active compounds. The controlled delivery may be exercised by selecting appropriate macromolecules (for example, polyester, polyamino acids, polyvinyl pyrrolidone, ethylenevinylacetate, methylcellulose, carboxymethylcellulose, and protamine sulfate) and the concentration of macromolecules as well as the methods of incorporation in order to control release.

Another possible method to control the duration of action by controlled release preparations is to incorporate the present compound into particles of a polymeric material such as polyesters, polyamino acids, hydrogels, poly (lactic acid) or ethylene vinylacetate copolymers. Alternatively, instead of incorporating the active compounds into these polymeric particles, it is possible to entrap the active compounds in microcapsules prepared, for example, by coacervation techniques or by interfacial polymerization, for example, hydroxymethylcellulose or gelatin-microcapsules and poly (methylmethacrylate) microcapsules, respectively, or in colloidal drug delivery systems, for example, albumin microspheres, microemulsions, nanoparticles, and nanocapsules or in macroemulsions. Such teachings are disclosed in *Remington's Pharmaceutical Science,* A. Oslo, Ed; 17th ed.; Mack: Easton, Pa., 1985.

After administration to a mammal by either the oral and parenteral route, a compound of formula (I) quickly breaks down in vivo at physiological pH to liberate taxol. Thus, the compounds of formula (I), because of their good antitumor activity and water solubility, will find use as a prodrug of taxol.

The present invention is illustrated by the following examples. However, it should be understood that the invention is not limited to the details of these examples. Proton nuclear magnetic resonance spectra (NMR) were measured at 500 MHz unless otherwise indicated for solutions in deuterochloroform (CDCl$_3$) and peak positions are expressed in parts per million (ppm) downfield from tetramethylsilane. The peak shapes are denoted as follows: s, singlet; d, doublet; t, triplet; q, quartet; m, multiplet; and b, broad.

EXAMPLE 1

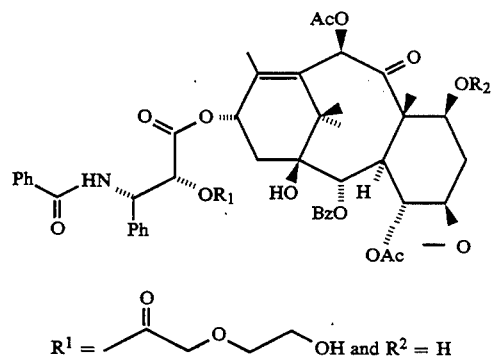

A solution of taxol (2 mg, 2.36 μmol) in pyridine (0.2 ml) was treated with diglycolic anhydride (5 mg, 42 μmol) and was stirred for 2 hours at 25° C. Then pyridine was azeotroped with benzene (3×), the residue was stirred with water for 20 minutes and extracted with CHCl$_3$. The organic phase was washed with brine, dried over Na$_2$SO$_4$ and the solvent was removed in vacuo. The residue was recrystallized from CHCL$_3$/benzene to give the title compound as a white solid; mp 150°–152° C.

1H NMR: δ1.14 (s, 3H, CH$_3$), 1.25 (s, 3H, CH$_3$), 1.68 (s, 3H, CH$_3$), 1.88 (m, 1H, CH$_2$), 1.94 (s, 3H, CH$_3$), 1.97 (s, 1H, OH), 2.23 (m, 1H, CH), 2.24 (s, 3H, CH$_3$), 2.40 (dd, J=9, 15 Hz, 1H, CH$_2$), 2.45 (s, 1H, OH), 2.48 (s, 3H, CH$_3$), 2.51 (ddd, J=7, 7, 15 Hz, 1H, CH$_2$), 3.82 (d, J=7H, 1H, CH), 4.07 (d, J=16.5 Hz, 1H, OCH$_2$), 4.14 (d, J=16.5 Hz, 1H, OCH$_2$), 4.21 (d, J=8.5 Hz, 1H, OCH$_2$), 4.23 (d, J=16.5 Hz, 1H, OCH$_2$), 4.29 (d, J=16.5 Hz, 1H, OCH$_2$), 4.32 (d, J=8 Hz, 1H, OCH$_2$), 4.44 (dd, J=7, 11 Hz, 1H, OCH), 4.98 (dd, J=2, 10 Hz, 1H, OCH), 5.62 (d, J=3 Hz, 1H, OCH), 5.69 (d, J=7 Hz, 1H, OCH), 6.07 (dd, J=2, 9.5 Hz, 1H, CHN), 6.28 (t, J=9 Hz, 1H, OCH), 6.30 (s, 1H, OCH), 7.11 (d, J=9.5 Hz, NH), 7.45 (m, 10H, aromatic), 7.61 (tt, J=1.5, 7.5 Hz, 1H, aromatic), 7.74 (dd, J=1.5, 7 Hz, 2H, aromatic), 8.14 (dd, J=1.5, 7 Hz, 2H, aromatic).

HRMS for C$_{51}$H$_{55}$NO$_{18}$Cs (M+Cs+): calcd 1102.2473, found 1102.2440.

EXAMPLE 2

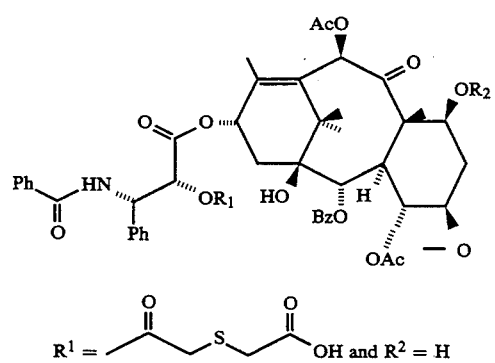

A solution of taxol (2 mg, 2.36 μmol) in pyridine (0.2 ml) was treated with thiodiglycolic anhydride (8 mg, 60 μmol) and a catalytic amount of DMAP. After stirring at 25° C. for 12 hours pyridine was azeotroped with benzene (3×), the residue was stirred with water for 20 minutes and extracted with CHCL₃. The organic phase was washed with brine, dried over Na₂SO₄ and the solvent was removed in vacuo. The residue was purified by preparative TLC (10% MeOH in CH₂Cl₂, Rf=0.35) to give the title compound (1.6 mg, 63%) as a white solid.

¹H NMR: δ1.11 (s, 3H, CH₃), 1.21 (s, 3H, CH₃), 1.68 (s, 3H, CH₃), 1.88 (m, 1H, CH₂), 1.94 (s, 3H, CH₃), 2.10 (m, 1H, CH₂), 2.23 (s, 3H, CH₃), 2.37 (m, 1H, CH₂), 2.48 (s, 3H, CH₃), 2.55 (m, 1H, CH₂), 3.18 (d, J=15 Hz, 1H, SCH₂), 3.31 (d, J=14.5 Hz, 1H, SCH₂), 3.37 (d, J=14.5 Hz, 1H, SCH₂), 3.49 (d, J=15 Hz, 1H, SCH₂), 3.80 (d, J=7 Hz, 1H, CH), 4.21 (d, J=8 Hz, 1H, OCH₂), 4.2 (d, J=8 Hz, 1H, OCH₂), 4.44 (dd, J=7, 11 Hz, 1H, OCH), 4.99 (d, J=7.5 Hz, 1H, OCH), 5.48 (d, J=3.5 Hz, 1H, OCH), 5.69 (d, J=7 Hz, 1H, OCH), 6.04 (d,d, J=3.5, 9 Hz, 1H, CHN), 6.25 (t, J=9 Hz, 1H, OCH), 6.29 (s, 1H, OCH), 7.42 (m, 10H, aromatic), 7.61 (m, 1H, aromatic), 7.82 (dd, J=1, 8.5 Hz, 2H, aromatic), 8.15 (d, J=7 Hz, 2H, aromatic), 8.62 (s, br, 1H, OH).

HRMS for C₅₁H₅₄NO₁₇S (M−H⁺): calcd 984.3112; found 984.3123.

EXAMPLE 3

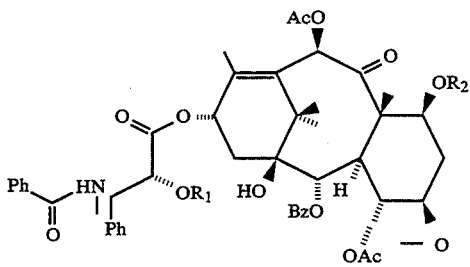

A solution of 2'-thiodiglycolic taxol (EXAMPLE 2) (30.5 mg. 31 μmol) in MeOH (2 ml) was added to a solution of OXONE ® (Aldrich Chemicals, Milwaukee, Wis.; 37 mg, 60 μmol) in phosphate buffer (pH=5) at 0° C. The solution was warmed to ambient temperature and stirred for 12 hours. Then MeOH was evaporated, the water phase extracted with CHCL₃ (3×), washed with brine, dried over Ha₂SO₄ and the solvent was removed in vacuo. After having subjected to preparative TLC (SiO₂, 16% MeOH in CH₂CL₂), the title sulfoxide derivative 3a and the sulfone derivative 3b were isolated as beige powders. 3a:Rf=0.24 (16% MeOH in CH₂CL₂), (4.2 mg, 14%).

HRMS for C₅₁H₅₄NO₁₈SCs (M−H+, 2 Cs+): calcd 1266.1170, found 1266.1130.

3b:Rf=0.36 (16% MeOH in CH₂CL₂), (15.4 mg, 50%).

EXAMPLE 4

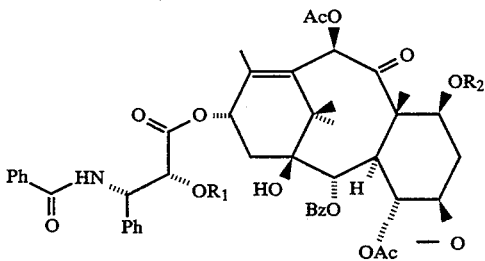

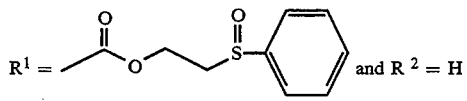 and R² = H

To a solution of 2-phenylsulfone-ethanol (560 mg, 3 mmol) and triphosgene (297 mg, 1 mmol) in CH₂Cl₂ was added 1 eq. of pyridine (243 μl, 3 mmol) at 0° C. After stirring for 5 minutes the solution was warmed to ambient temperature and stirred for another 45 min. Three eq. of this solution (88 μl, 58.5 μmol) were added to a solution of taxol (10 mg. 11.7 μmol) in CH₂CL₂. At 0° C., pyridine (5 μl, 58 μmol) was added. The solution was stirred at 25° C. for 12 hours, then washed with diluent. HCL (pH=3) and brine. The organic phase was dried over Na₂SO₄, the solvent removed in vacuo and the residue purified by preparative TLC (5% MeOH in CH₂CL₂, Rf=0.48) to give the title compound as a white solid (3 mg. 25%).

¹H NMR: δ1.14 (s, 3H, CH₃), 1.25 (s, 3H, CH₃), 1.68 (s, 3H, CH₃), 1.88 (m. 1H, CH₂), 1.91 (s, 3H, CH₃), 2.22 (m, 1H, CH₂), 2.23 (s, 3H, CH₃), 2.39 (dd, J=9.5, 15 Hz, 1H, CH₂), 2.43 (s, 3H, CH₃), 2.48 (s br, 1H, OH), 2.55 (m, 1H, CH₂), 3.47 (t, J=6.5 Hz, 2H, OCH₂), 3.81 (d, J=7 Hz, 1H, OCH), 4.20 (d, J=8.5 Hz, 1H, OCH₂), 4.32 (d, J=8.4 H₂, 1H, OCH₂), 4.44 (dd, J=7, 11 Hz, 1H, OCH), 4.48 (t, J=6.5 Hz, 2H, SCH₂), 4.97 (d, J=7.5 Hz, 1H, OCH), 5.38 (d, J=3 Hz, 1H, OCH), 5.69 (d, J=7 Hz, 1H, OCH), 5.97 (dd, J=3, 9.5 Hz, 1H, CHN), 6.28 (t, J=9 Hz, 1H, OCH), 6.29 (s, 1H, OCH), 6.82 (d, J=9.5 Hz, 1H, NH).

EXAMPLE 5

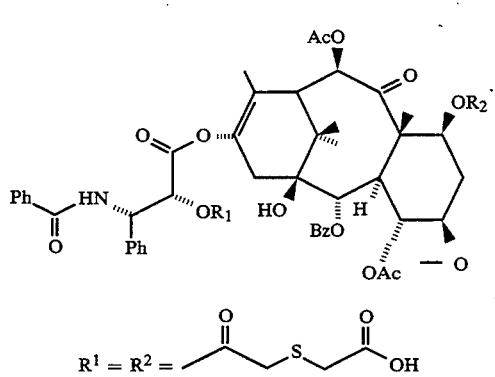

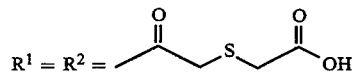

A solution of taxol (4 mg. 4.7 μmol) in 0.2 ml dry pyridine was treated with thiodiglycolic anhydride (6.6 mg, 50 μmol) and DMAP (1.2 mg, 10 μmol). After stirring at 25° C. for 12 hours, the solvent was evaporated and the residue was stirred in water for 20 minutes. The precipitation was filtered, dissolved in CHCL₃, washed with brine and dried over Na₂SO₄. The solvent was removed in vacuo and the residue was purified by preparative TLC (30% MeOH in CH₂CL₂) to give the title compound as a white solid (3.3 mg, 64%).

¹H NMR: δ1.14 (s, 3H, CH₃). 1.26 (s, 3H, CH₃), 1.80 (s, 3H, CH₃), 1.88 (m, 1H, CH₂), 1.94 (9s, 3H, CH₃), 2.14 (s, 3H, CH₃), 2.22 (m, 2H, CH₂), 2.39 (s, 3H, CH₃), 2.59 (m, 1H, CH₂), 3.41 (m, 8H, SCH₂), 3.87 (d, J=7 Hz, 1H, CH), 4.15 (d, J=8.5 Hz, 1H, CH₂), 4.30 (d, J=8.5 Hz, 1H, CH₂), 4.95 (d, J=9 Hz, 1H, CH), 5.62 (m, 3H, CH), 5.99 (dd, J=5, 9 Hz, 1H, CH), 6.15 (m, 1H, CH). 6.17 (s, 1H,

CH). 7.45 (m, 10H, aromatic), 7.62 (t, J=7.5 Hz, 1H, aromatic), 7.81 (dd, J=1.5, 8 Hz, 2H, aromatic), 8.01 (d, J=7.5 Hz, 2H, aromatic), 8.64 (br s, 2H, OH).

HRMS for $C_{55}H_{58}NO_{20}S_2$ (M−H+): calcd 1116.2994, found 1116.3061.

EXAMPLE 6

Tablet Formulation

The following ingredients are combined in the following proportions by weight:

| | |
|---|---|
| taxols | 20 |
| lactose | 200 |
| hydroxypropylmethylcellulose | 5 |
| sodium starch glycolate | 20 |
| magnesium stearate | 5 |

The mixture is blended to a uniform powder and compressed into tablets in measured volumes corresponding to 250 mg by weight to yield tablets of desired potency.

EXAMPLE 7

Capsule Formulation

The following ingredients are combined in the following proportions by weight:

| | |
|---|---|
| taxols | 50 |
| cornstarch | 447 |
| magnesium stearate | 3 |

The mixture is thoroughly blended so as to obtain a uniform powder. The resulting mix (500 mg fill weight) is filled into hard gelatin capsules of a suitable size so as to obtain capsules of desired potency.

EXAMPLE 8

Cytotoxicity

The taxol derivatives of the present invention are particularly useful for the treatment of the same tumors for which taxol has been shown active, including lung tumor, melanoma, leukemia, colon cancer and breast cancer.

The ability of the compounds to inhibit tumors has been tested by in vitro studies using various cancer cell lines.

Tumor or normal cells were cultured in 96-well plates with the test compound in 200 μl of RPMI supplemented with 10% fetal bovine serum (Hyclone, Salt Lake City, Utah) at 37° C. in a humidified atmosphere containing 5% $CO_2$ in air for 72 hours. Sulforhodamine B dissolved in 1% acetic acid was added, and the plates were incubated for 30 minutes at ambient temperature, washed with 1% acetic acid, and blotted. To the airdried plates were added 100 μl of 10 μM unbuffered TRIS base (pH 10.5) with shaking. The optical densities of the plates were measured with a microplate reader (Molecular Devices Thermomax) at 540 nm. The concentration of compound required to reduce the absorbance to 50% of control samples was recorded as $IC_{50}$.

Results of the tests performed on several selected derivatives of taxol using established normal or cancer cell lines are summarized in the table.

| CYTOTOXICITY OF TAXOL DERIVATIVES ($IC_{50}[M]$) | | | | | | |
|---|---|---|---|---|---|---|
| Cell Line | Taxol | Example 1 | Example 2 | Example 3a | Example 3b | Example 4 |
| NHDF | 2.08e-4 | 1.03e-4 | 5e-5 | 5e-5 | 1.9e-7 | 5e-5 |
| HLF-1 | 6.3e-5 | 5.95e-5 | 3.1e-6 | 2.5e-5 | 1.3e-5 | 6.3e-6 |
| W1-38 | 6.06e-5 | 5.19e-5 | 1.3e-5 | 2.5e-5 | 1.3e-5 | 5e-5 |
| CHO | 5.35e-5 | 1.01e-4 | 5e-5 | 1e-4 | 1e-4 | 1e-4 |
| SK-MEL-28 | 1e-4 | 1e-4 | 1e-4 | 1e-4 | 1e-4 | 1e-4 |
| CAPAN-1 | 9.8e-8 | 9.8e-8 | 1.9e-7 | 8.7e-7 | 1.9e-7 | 9.8e-8 |
| H322 | 1.22e-4 | 2.05e-4 | 3.1e-6 | 8.3e-6 | 5e-6 | 6.3e-6 |
| MCF-7 | 6.44e-5 | 3.57e-4 | 1e-4 | 3.92e-5 | 6.1e-5 | 7e-5 |
| BT-549 | 4.46e-5 | 5.14e-5 | 1.6e-5 | 9.8e-8 | 9.8e-8 | 1e-9 |
| OVCAR-3 | 9.8e-8 | 9.8e-8 | 3.9e-7 | 9.8e-8 | 9.8e-8 | 9.8e-8 |
| HT-29 | 9.8e-8 | 1e-8 | 1.9e-7 | 9.8e-8 | 9.8e-8 | 9.8e-8 |
| SIHA | 1.11e-3 | 1.12e-3 | 5e-5 | 2.5e-5 | 5e-5 | 3.1e-5 |
| 786-0 | 1.84e-7 | 1.53e-7 | 6.3e-6 | 1.5e-7 | 1.3e-7 | 2.5e-6 |
| PC-3 | 6.91e-5 | 6.51e-5 | 1e-4 | 5e-5 | 5e-5 | 5e-5 |
| HL-60 | 1e-14 | 1e-14 | 1e-14 | 1e-14 | 1e-14 | 1e-14 |
| MOLT-4 | 1e-14 | 1e-14 | 1e-14 | 1e-14 | 1e-14 | 5e-12 |

NHDF: Normal human dermal fibroblast (available from Clouelics Corp., San Diego, Calif.); HLF-1: Normal human diploid lung; W1-38; Normal human diploid lung; CHO; Chinese hamster ovary; SK-MEL-28: Melanoma; CAPAN-1: Pancreatic carcinoma; H322: lung carcinoma; MCF-7; Breast carcinoma; BT-549; Human breast ductal carcinoma; OVCAR-3: Human ovarian carcinoma; HT-29: Human adenocarcinoma, colon; SIHA: Human squamous carcinoma crvx; 786-0: Human perirenal cell adenocarci; PC-3: Human prostate adenocarcinoma; HL-60: Human promyelomic leukemia; MOLT-4: Human T-cell leukemia. All cell lines except NHDF are available from the American Tissue Culture Collection, Rockville, Md.

Solubility

Some representative taxol derivatives of the present invention show improved water solubility as compared to taxol which is essentially insoluble in water. Where the compounds of formula (I) wherein Z is OH are not water soluble, their base salts can be prepared as hereinbefore indicated and they can form normal aqueous solutions up to about 1% concentration.

Where the compounds of formula (I) which contain an amino or N,N-dialkylamino group are not water soluble, their acid salts can be prepared as hereinbefore indicated and they can form normal aqueous solutions up to about 1% concentration.

The above test results indicate that the taxol derivatives of the present invention exhibit excellent antitumor activity. These compounds, therefore, are useful antitumor agents due to their biological activity and their increased water solubility as compared to taxol.

The invention now being fully described, it will be apparent to one of ordinary skill in the art that many changes and modifications can be made without departing from the spirit or scope of the invention.

EXAMPLE 9

Synthesis of the Compounds of Table 1 A

Preferred reagents and conditions for the synthesis of compounds 3–12 of Table 1 A from taxol (1) are indicated as follows:

(a) Compound 3: 1.1 equivalents of diglycolic anhydride in pyridine at 25° C. for 2 hours (yield 75%);

(b) Compound 4: 2.0 equivalents of thiodiglycolic anhydride in pyridine at 25° C. for 4 hours (67%);

(c) Compound 5: same as (b), then 3.0 equivalents of Oxone, $CH_3OH/H_2O$, 25° C., 12 hours (65% overall);

(d) Compound 6: same as (b), then $CH_2N_2$, 3.0 equivalents of Oxone, $CH_3OH/H_2O$, 25° C., 2 hours (32% overall);

(e) Compound 7: 1.2 equivalents of (2-thiophenyl)ethyl chloroformate, $(C_2H_5)_3N,CH_2Cl_2$, 25° C., 2 hours (94%);

(f) Compound 8: same as (e), then 3.0 equivalents Oxone, $CH_3OH/H_2O$, 25° C. (75% overall);

(g) Compound 9: 1.2 equivalents (2-p-nitrothiophenyl)ethyl chloroformate, $(C_2H_5)_3N,CH_2C_2$, 25° C., then Oxone, (74% overall);

(h) Compound 10: same as (g), then Oxone, followed by sodium dithionite, $C_2H_5OH,H_2O$ (62% overall);

(i) Compound 11: 10.0 equivalents diglycolic anhydride pyridine (87%);

(j) Compound 12: 10.0 equivalents thiodiglycolic anhydride, 4-dimethylaminopyridine (as catalyst), $CH_2Cl_2$ (29%).

Solubilities:

(k) Water solubility of each of the indicated compounds was determined by combining 2.0 mg sample with 1.0 ml $D_2O$ and sonicating for 15 min. The resulting mixture was centrifuged for 20 minutes and the supernatant saturated solution was analysed by $^1H$ NMR spectroscopy using a Bruker AMX-400 instrument and methanol or pyridine as internal standard. The concentration of the compound was determined by comparing several signals with the $CH_3$ signal of methanol or the NCH signal of pyridine.

(l) The detection limit for the determination of the solubilities of compounds 8, 9, and 10, as determined by diluting samples of compound 5, was found to be 0.10 mg ml$^{-1}$.

(m) The relatively high concentrations found for compound 5 during the solubility measurements are due to the formation of hydrogels, presumably caused by the formation of micelles or related aggregates.

Half Life:

The half-life ($t_{\frac{1}{2}}$) of the protaxol is defined as the time in minutes at which 50% taxol release was observed at 37° C.

Toxicities Reported in Table 1 B

The cytotoxicities were determined using the sulphorhodamine B assay method (Skehan, P. et al. J. Nat. Canc. Inst. 82, 1107 (1990)).

$IC_{50}[M]$ is defined as the molarity at which 50% of tumour cell viability was observed after 72 hours of exposure under standard tissue culture conditions.

EXAMPLE 10

Tubulin polymerization-depolymerization experiments

Tubulin polymerization-depolymerization experiments with taxol and designed protaxol 5 are illustrated in FIG. 3. $CaCl_2$-promoted depolymerization of microtubules was suppressed by taxol and protaxol 5 (after taxol release).

METHODS.

These measurements may be conducted at 37° C. following a recently developed procedure described by R. Merlock and W. Wrasidlo (Analytical Biochemistry, 1993). In each case 1.0 mM GTP may be employed to promote initial polymerization of tubulin.

A: control: Tubulin (1.0 mg/mL) alone; CaCl2 (0.25 mM) added after 16 minutes caused depolymerization of microtubules.

B: Tubulin (1.0 mg/mL) with taxol (10-6M); CaCl2 (0.25 mM) added after 16 minutes did not cause depolymerization.

C: Tubulin (1.0 mg/mL) with protaxol 5 (10-6M); CaCl2 (0.25 mM) added after 16 minutes caused depolymerization of microtubules.

D: Tubulin (1.0 mg/mL) with protaxol 5 (10-6M) after release of taxol (as determined by HPLC, essentially quantitative conversion).

Addition of the $CaCl_2$ solution is designated by the symbol (a).

EXAMPLE 11

Kinetics of Taxol Release from Compound 5

Kinetics of taxol release from protaxol 5 in aqueous buffer solutions at various pH's and temperatures is illustrated in FIG. 2A. Kinetics of taxol release from protaxol 5 in human blood plasma and pH 7.4 buffer solution at 37° C. is illustrated in FIG. 2B. Although it is quite stable at 20° C. and in pH 7.0 buffer solution, protaxol 5 is converted to taxol in human plasma at 37° C. with a half-life of ~100 min.

Conditions in FIG. 2A:

▲ pH 7.0, 20° C.; O, pH 7.0, 37° C.; ●, pH 7.5, 37° C.; □, pH 8.0, 37° C.; ■, pH 9.0, 37° C.

METHODS for FIG. 2A:

Protaxol 5 was dissolved in dimethylsulphoxide (DMSO) at 25° C. and immediately added to the appropriate phosphate buffer solution at the specified temperature. Aliquots were analysed using a Waters Maxima system HPLC instrument equipped with auto-injector (3.9×300 mm $C_{18}$ column equipped with a precolumn; flow rate, 1.5 ml min$^{-1}$; eluant, gradient A–B, where A is 80% 100 mM ammonium acetate, buffer pH 6.0, and B is 100% methanol; ultraviolet detector). The percent taxol released was determined from the relative areas of the peaks corresponding to protaxol 5 and taxol (the conversion was clean, and it was assumed that the two compounds have equal molar extinction coefficients).

Method for FIG. 2 B:

Protaxol 5 and N-cyclohexylbenzamide (as internal standard) were dissolved in acetonitrile and immediatley added to human plasma or phosphate buffer at pH 7.4. Samples of protaxol 5 were incubated in each medium for specified times and then extracted with ethyl acetate as described by S. M. Longnecker, et al., Cancer Treat. Rep. 71, 53 (1987). Solvent was removed and the residue dissolved in acetonitrile and analysed by HPLC as already described. The peak areas for compound 5 and taxol were normalized to that of the internal standard using a calibration curve.

Conditions in FIG. 2B:

▲ percent protaxol 5 remaining in pH 7,4 phosphate buffer; ●, percent taxol released in pH 7.4 phosphate buffer; △, percent protaxol 5 remaining in human plasma; ○, percent taxol released in human plasma.

We claim:

1. A compound of the formula:

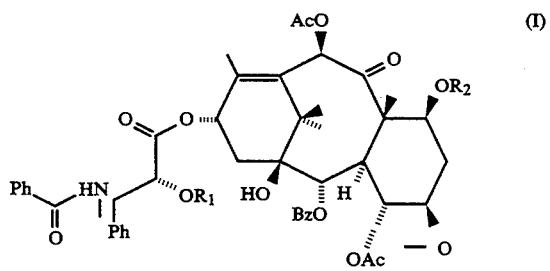

wherein $R^1$ and $R^2$ are each H or a radical selected from the group consisting of —CO—$(CH_2)_m$—X—$(CH_2)_n$—COZ and —COO—$(CH_2)_o$—Y—Ar, wherein m, n, and o are each an integer of 1 to 3; X is O, S, NH, SO, or $SO_2$; Y is S, SO or $SO_2$; Ar is phenyl or substituted phenyl wherein the substituent is halo, amino, nitro, or N,N-diallkylamino having 1 to 4 carbons in each of the alkyl groups; and Z is OH; with the proviso that at least one of $R^1$ and $R^2$ is not hydrogen, or a pharmaceutically acceptable salt thereof.

2. The compound according to claim 1, wherein $R^2$ is H.

3. The compound according to claim 2, wherein $R^1$ is —CO—$(CH_2)_m$—X—$(CH_2)_n$—COZ.

4. The compound according to claim 3, wherein each of m and n is 1.

5. The compound according to claim 3, wherein X is S.

6. The compound according to claim 2, wherein $R^1$ is —COO—$(CH_2)_o$—Y—Ar.

7. The compound according to claim 6, wherein o is 2.

8. The compound according to claim 7, wherein Ar is phenyl.

9. The compound according to claim 1, wherein each of $R^1$ and $R^2$ is —CO—$(CH_2)_m$—X—$(CH_2)_n$—COZ.

10. The compound according to claim 9, wherein each of m and n is 1.

11. The compound according to claim 10, wherein X is S.

12. A pharmaceutical composition comprising a tumor inhibiting effective amount of the compound according to claim 1, together with a pharmaceutically acceptable carrier or diluent.

13. A method for inhibiting tumors in a mammal which comprises administering to the mammal a tumor inhibiting effective amount of the compound according to claim 1.

* * * * *